(12) United States Patent
Corbett

(10) Patent No.: US 11,745,090 B1
(45) Date of Patent: Sep. 5, 2023

(54) APPARATUS FOR EVALUATING AND IMPROVING MANUAL DEXTERITY

(71) Applicant: Julie J. Corbett, Cold Spring, NY (US)

(72) Inventor: Julie J. Corbett, Cold Spring, NY (US)

( * ) Notice: Subject to any disclaimer, the term of this patent is extended or adjusted under 35 U.S.C. 154(b) by 1201 days.

(21) Appl. No.: 16/152,137

(22) Filed: Oct. 4, 2018

Related U.S. Application Data

(60) Provisional application No. 62/567,972, filed on Oct. 4, 2017.

(51) Int. Cl.
*A63F 9/06* (2006.01)
*A61B 5/11* (2006.01)

(52) U.S. Cl.
CPC .......... *A63F 9/0666* (2013.01); *A61B 5/1124* (2013.01)

(58) Field of Classification Search
CPC .................................................. A63F 9/0666
USPC ........................................................ 434/258
See application file for complete search history.

(56) References Cited

U.S. PATENT DOCUMENTS 8,646,780 B1 * 2/2014 Spencer ................ A63F 9/0247
273/457

* cited by examiner

*Primary Examiner* — Kesha Frisby
(74) *Attorney, Agent, or Firm* — Blank Rome LLP

(57) ABSTRACT

A manual dexterity device has a base and a lid. The base includes a bottom and three side walls that form an open top. The lid is received on said base at the top opening and is movable between a closed position in which the lid closes the top opening and an opened position in which the top opening is open. A plurality of slots are arranged on the lid in rows and columns. The slots are configured to receive test or control objects that test the manual dexterity of a user. Test objects passing through any of said one or more slots are received in the base.

7 Claims, 4 Drawing Sheets

| INITIALS | OCCUPATION | AGE | SEX | DOM | HAND INJURY | DX | NET TIME R/L | R HAND DROPPED/ SCORE | L HAND DROPPED/ SCORE | RETEST NET TIME R/L | RETEST R HAND DROPPED/ SCORE | RETEST L HAND DROPPED/ SCORE | PERCENTAGE OF CHANGE IN NET TIME | PERCENTAGE OF CHANGE IN PENALTY SCORE |
|---|---|---|---|---|---|---|---|---|---|---|---|---|---|---|
| | | | | | | | 55/30 | 4/75 | 2/40 | 41/27 | 4/61 | 4/47 | 25.45 | 18.65 |
| | | | | | | | 45/39 | 2/55 | 2/49 | 36/34 | 2/46 | 0/34 | 20 | 16.36 |
| | | | | | | | 60/48 | 0/60 | 0/48 | 37/35 | 0/37 | 3/50 | 38.33 | 38.33 |
| | | | | | | | 62/36 | 6/92 | 6/66 | 46/32 | 4/66 | 3/47 | 25.81 | 28.26 |
| | | | | | | | 39/36 | 4/58 | 0/36 | 37/44 | 4/57 | 0/44 | 5.13 | 3.39 |
| | | | | | | | 25/27 | 0/25 | 0/27 | 22/23 | 2/32 | 0/23 | 14.81 | 100 |
| | | | | | | | 29/35 | 0/29 | 2/45 | 23/34 | 0/23 | 0/34 | 2.85 | 100 |
| | | | | | | | 33/43 | 2/43 | 2/53 | 28/33 | 0/28 | 0/33 | 23.26 | 100 |
| | | | | | | | 36/52 | 2/46 | 4/72 | 25/37 | 1/30 | 5/62 | 28.85 | 93.06 |
| | | | | | | | 38/41 | 2/48 | 2/51 | 30/37 | 5/55 | 3/52 | 9.76 | 94.12 |
| | | | | | | | 43/55 | 0/43 | 0/55 | 33/35 | 0/33 | 0/35 | 36.36 | 100 |
| | | | | | | | 26/27 | 2/36 | 2/37 | 24/29 | 2/34 | 2/39 | -7.41 | 94.59 |
| | | | | | | | 22/47 | 0/22 | 3/62 | 21/59 | 5/46 | 4/79 | -25.53 | 93.55 |
| OVERALL AVERAGE | | | | | | | | | | | | | 15.21 | 67.72 |

FIG. 7

APPARATUS FOR EVALUATING AND IMPROVING MANUAL DEXTERITY

BACKGROUND OF THE INVENTION

Related Applications

This application claims the benefit of U.S. Provisional Application No. 62/567,972, filed Oct. 4, 2017, the entire contents of which are incorporated herein by reference.

Field of the Invention

The "present invention" relates to an apparatus for evaluating and improving manual dexterity. More specifically, the invention relates to a palm to finger translation and targeted coin placement test requiring functional oblique wrist motion.

BACKGROUND OF THE RELATED ART

There is a variety of reliable and valid dexterity tests in the armamentarium of Occupational Therapy, with the exception of In Hand Manipulation (HM) translation norms as well as a reliable and valid test for palm to finger translation. Many Occupational and Physical Therapists and Certified Hand Therapists use activity drills for shift, rotation and translation of coins from finger tips to palm and palm to fingertips into a single piggy bank slot in hand therapy practices. Pediatric therapists have investigated the developmental skill of "squirreling" or in-hand manipulation, consisting of shift, rotation, and translation of small objects as well as establishing norms for this population. Research has contributed to our understanding of the biomechanics of the wrist and functional oblique wrist motions or the Dart Thrower's Motion (DTM). Research has been done on the role of wrist proprioception in the sensorimotor system and its role in neuromuscular control and stability for hand function. The wrist is regarded as the keystone for efficient and accurate hand placement in space.

Recent studies investigate the role of the wrist and hand sensorimotor system and the wrist functional oblique motions or dart throwing motion plane in activities of daily living (ADLs). Fine motor skills are dependent on the manipulation and voluntary placement of objects to attain meaningful ADL independence. Motor Component Analysis (MCA) identifies the source of dysfunction and is fundamental to the OT/PT hand therapy diagnostic and treatment process. Methods of testing In Hand Manipulation (IHM) can be broadly classified into 3 categories characterized by simulating performance of voluntary manipulation and placement, of small objects such as coins, pellets, buttons, nuts and bolts, as well as, pegboard tasks. A literature review conducted and a panel of experts surveyed suggest there is a gap in standardized assessment tools for measuring and observing recovery of palm to fingertip shift, rotation, and translation for targeted placement of an object with proprioceptive input from the wrist in the hand injured population.

SUMMARY OF THE INVENTION

The present invention is a test that integrates palm to fingertip translation of coins with various wrist Range of Motion (ROM) components. This test fills a gap in the continuum of hand manipulation/dexterity evaluation and documentation of qualitative and quantitative skill acquisition. The present invention has been used in a clinic setting on a test-retest basis with volunteer participants.

A targeted coin test approaches the problem of assessing palm to finger shift, rotation and translation of a coin or small object with ulnar digit stabilization and wrist functional oblique motion requirements in recovery of meaningful, real-life tasks.

BRIEF DESCRIPTION OF THE FIGURES

FIG. 7 is an example of test results.

DETAILED DESCRIPTION OF THE PREFERRED EMBODIMENTS

Figure 1:
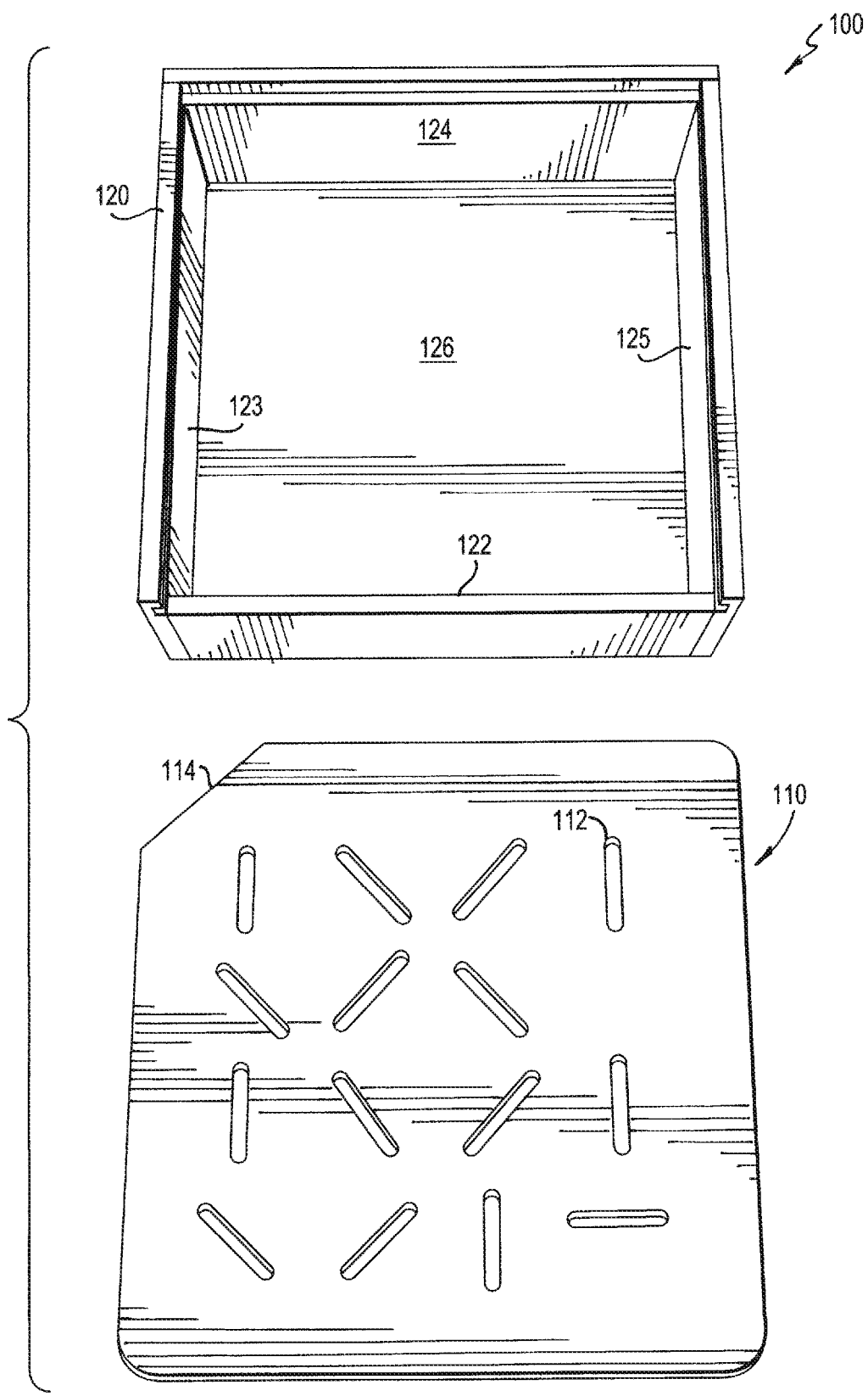
FIG. 1 shows an exploded top view of the base with a lid in accordance with an embodiment of the invention.

In describing the preferred embodiments of the present invention illustrated in the drawings, specific terminology is resorted to for the sake of clarity. However, the present invention is not intended to be limited to the specific terms so selected, and it is to be understood that each specific term includes all technical equivalents that operate in a similar manner to accomplish a similar purpose.

This specific fine motor skill of in hand manipulation (IHM) can be evaluated by speed of execution and quality in test-retest format. Turning to the drawings, the FIGS. 1-6 show the present invention comprises an evaluation and therapy apparatus, or device, 100 for evaluating and improving manual dexterity. The device 100 is a box having a flat sliding lid 110 and a collection base 120. The lid 110 comprises a flat board having a plurality of openings 112 in the form of elongated slots arranged in columns and rows. Each slot 112 is at a different angle on the board and is sized and shaped to be slightly larger than the test or control object, here a coin such as a U.S. penny or quarter. The base 120 collects the coins once they are dropped through the slots 112, so that the total number of coins that successfully pass through the slots can be counted.

This preferred embodiment of a collection base 120 has four side walls 122, 123, 124, 125 and a bottom 126, to define an interior central space. The sides or walls include a front side wall 122, left side wall 123, rear side wall 124, and right side wall 125. The side walls 122-125 are elongated and can have the shape of a rectangle, and extend 2 inches vertically upright and orthogonal to the bottom 126, which is substantially horizontal. In this manner, the base 120 can receive and collect coins that pass through the lid 110. The base 120 has an open top with a top opening. Anti-slip corner pads are placed underneath the bottom four corners of the base 120 to prevent slippage. The lid 110 is received at the top opening of front side wall 122 to form a closed box.

Figure 5:
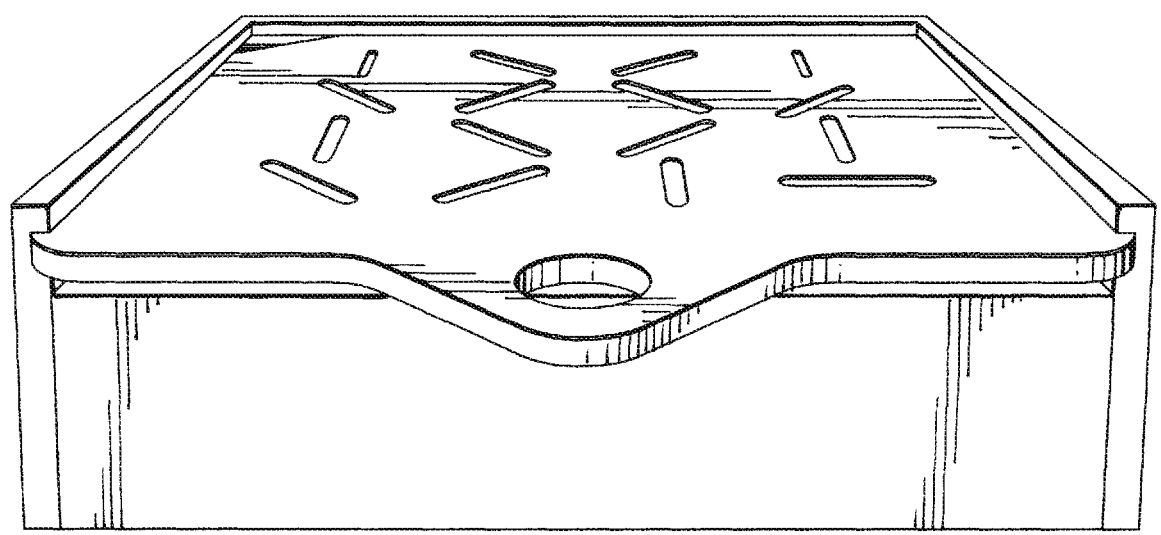
FIG. 5 is a side perspective view of the base with the lid.

The left, rear and right side walls 123, 124, 125 of the collection base are taller than the front side wall 122, and have a groove or channel 128 (FIG. 5). The channel 128 provides an approximately ⅜ inch indentation for slidably and removably receives the lid 110. In the left and right walls 123, 125, the channel 128 extends from the front to the rear of the base 120. In the rear wall 124, the channel 128 is optional and can extend from the left to the right of the base 120. The top, central rear wall can be fitted with a fastening device such as a vertical spring plunger to secure the lid 110 when the lid is in the rear channel. Thus, the channels 128 in each of the left, rear and right walls 123, 124, 125 are aligned with each other to form a single continuous channel 128. The front wall 122 does not have a channel, though can have an opening through which the lid 110 passes if the front wall 122 is designed to have the same height as the left, rear and right walls 123, 124, 125. The bottom of the channel 128 supports the lid 110 and prevents the lid 110 from inadvertently falling into the center of the base 120. The channels 128 are elongated with a longitudinal axis that is substantially parallel to the top of the respective wall 123-125.

Figure 6:
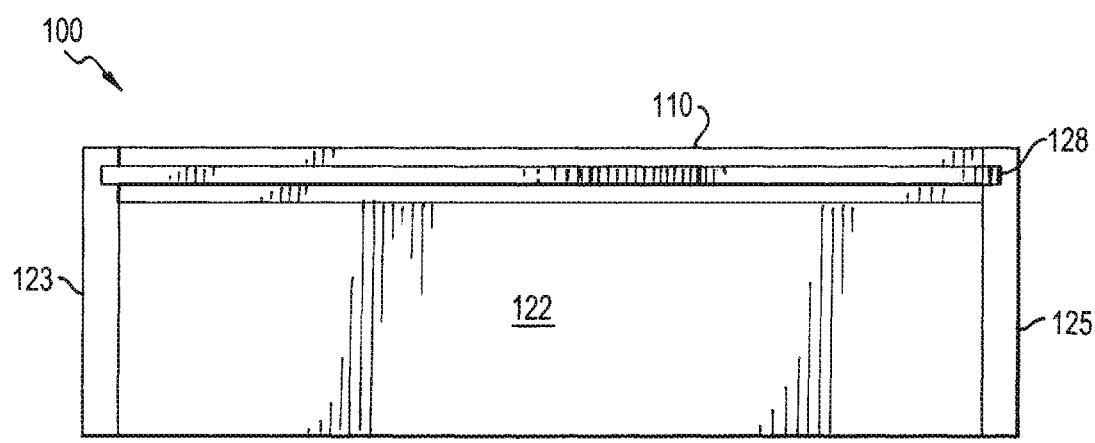
FIG. 6 is a side view of the base with the lid.

Thus, as best shown in FIGS. 5, 6, the lid 110 slides over the top of the front wall 122 and into and out of the grooves or channels 122 in the left, rear and right side walls 123, 124, 125. The channels 128 are recessed from the top edge at the perimeter of the base to secure placement of the lid 110 on the collection base. The channels 122 are aligned with the top of the front side wall 122 so that the lid 110 can easily slide over the front side wall 122 without obstruction. Thus, the outer perimeter edge of the lid 110 is received in the channel 128. Specifically, the left edge of the lid is received in the channel 128 extending along the left side wall 123, the rear edge of the lid is received in the channel 128 extending along the rear wall 124, and the right edge of the lid is received in the channel 128 extending along the right wall 125. The amount of edge received in the channel 128 is minimized (approximately ⅜ inch) to maximize the area for the slots 112 to be placed.

Accordingly, the collection box 100 has an opened position and a closed position. In the closed position, the lid 110 is received in the channel 128 and engaged with the base 120. The lid 110 is in a plane that is substantially parallel to a plane of the bottom 126, and substantially orthogonal to the side walls 122-125. In that position, the test can be performed and coins will be collected by the base 120. In the opened position, the lid 110 is removed from the base 120. In that position, the tester or user can remove and/or count the number of coins collected by the base 120, and determine the user's score on the test or exercise.

Figure 2:
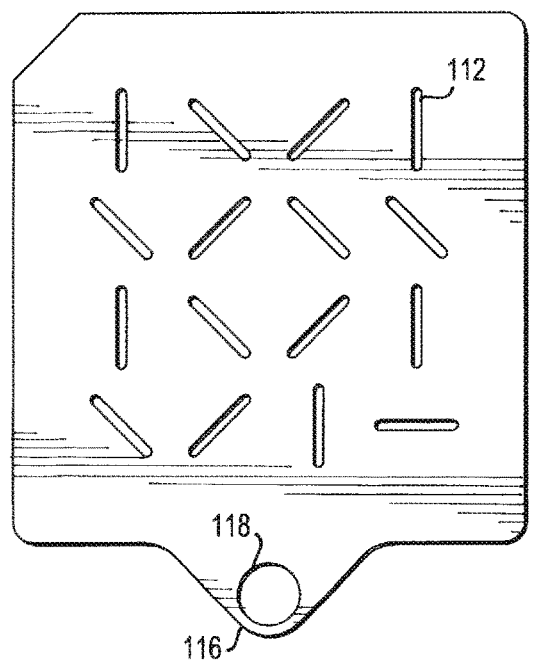
FIG. 2 is an alternative embodiment of the lid.
Figure 3:
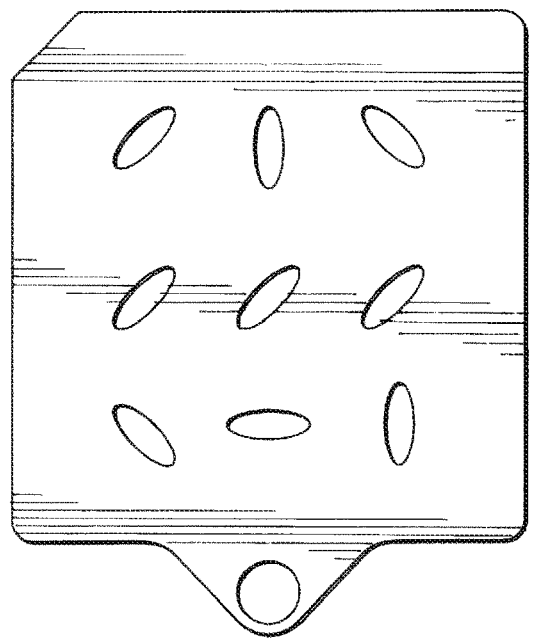
FIG. 3 is yet another alternative embodiment of the lid.
Figure 4:
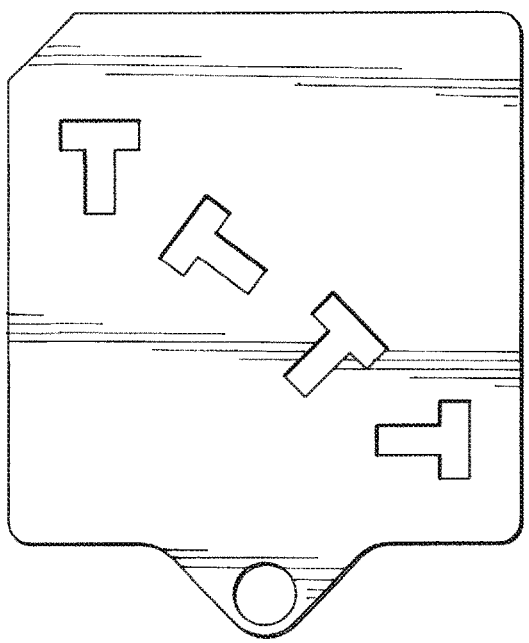
FIG. 4 is another alternative embodiment of the lid.

In one non-limiting illustrative embodiment of the invention, the base 120 measures 6.5"×6.5"×2" and the lid 110 measures 6.19"×6.38" and has 16 (sixteen) one-inch coin slots 112, with four (4) slots 112 in each of four (4) different rows and columns. The slots 112 can be approximately 0.13 inches in width. Of course, any suitable size, number and arrangement of slots 112 can be provided, such as shown in FIGS. 2-4. In addition, control objects of different sizes and shapes can be utilized other than coins with similarly-shaped openings other than slots such as but not limited to flat thin disc-shaped objects (e.g., bingo chips, coins, buttons), slightly widened flat disc-shaped objects (e.g., pellets, checkers, poker chips), non-uniform widened disc-shaped objects (e.g., flattened glass marbles, flat glass beads) or other shaped objects such as pills, nuts and/or bolts, and earrings. Small objects are preferably used so that several objects can be held in the hand at one time to test functional dexterity with items. In addition, the control objects can have different weights. The user can use control objects all having the same weight in a single test or stretching routine, or can use control objects having different weights. In one embodiment, the box 100 has a height of two (2) inches to provide consistency of table and chair position and to provide reliable and valid test results, though other suitable heights can be provided.

In addition, any suitable collection device can be utilized other than a base 120, or the lid 110 can be provided with hinged legs to raise it off of a surface that it is placed on, so that the coins fall directly onto a surface without any base. The hinged legs on the lid can fold for storage and reversal of lid. In the design process a minimal side wall height above the sliding channels for the sliding lid reduced obstacle and hindrance to the field of slots 112. The base is sufficiently larger than the area in which the slots are provided, so that the coins fall directly into the base. The base 120 and sliding lid 110 can be made of wood, cardboard, or plastic, or any other suitable material such as SINTRA (⅛ inch thick high density polyethylene or expanded PVC), which is strong and durable, easy to clean and machine and print. Three Dimensional (3 D) printing can also be an option for production.

As further shown in the figures, one corner 114 of the lid 110 can be angled or curved or any suitable indicator to indicate which hand is being tested. If the angled/curved corner 114 or suitable indicator is at the top right, the right hand is being tested. If the angled/curved corner or suitable indicator is at the top left, then the left hand is being tested. By having the base 120 and lid 110 square shaped, the lid 110 can be reversed or flipped over with respect to the base 120 so that the angled/curved corner 114 or suitable indicator of the lid 110 can be at the top left, or top right, of the base 120 (with respect to the embodiment of FIG. 1. Of course, any suitable indicator 114 can be used but printed symbols appear to compete with fine motor testing objective. In addition, a handle 116 can be formed at one side of the lid 110. The handle 116 can extend out from the side of the lid and optionally include an opening 118 to receive a person's finger, so that the tester or user can insert their finger into the opening and slide the lid from the base. In addition, the other corners can be slightly curved to facilitate the lid 110 being placed in the channels 128.

The directionality of the coin slots 112 is configured to require wrist functional oblique motion. The test requires a minimum of time for administration including a prerequisite demonstration of finger to palm shift, rotation and translation of 20 coins (such as U.S. pennies), reading of directions, initially 2 trials per hand, recording of scores and motor component analysis or observations of posture and upper extremity limb motions in palm to finger shift, rotation and translation of an object. All users are given verbal instruction to target at least 16 out of the 20 coins, all held in their hand at one time, into the slots. The opportunity for a practice trial eliminates the possible variable of unfamiliarity influencing task performance. Follow up retests require only one trial per hand.

To evaluate a user, a score is assigned. One score per hand is obtained on a scoring sheet similar to standardized scoring in the previously established dexterity test formats: 1) net time or speed, in seconds, to complete the test and 2) combined total of net time or speed plus 5 (five) second penalty per dropped coin provides score for qualitative score. A penalty of 5 seconds can also be assigned for any dropped coins or mistargeted coin as well as coin which slips from closed hand and added to net score to reflect accuracy of shift, rotation and translation of in hand manipulation (IHM) skill. Dropped coins are not to be picked up by the user. As an illustrative example of the present invention, if a user completes 16 slots 112 of the pattern in 55 seconds, using the right hand, the net time/speed is 55 (fifty-five) and considered a quantitative score. If the same user also dropped 4 coins in the right hand trial, a qualitative score can be determined by a calculation of net time/speed plus penalty of an addition of 5 seconds per dropped coin (55+20=75). FIG. 7 is an illustrative graph of 13 (thirteen) test-retest calculations.

In operation, the lid 110 is placed over the top of the base 120 to the closed position. The user holds 20 coins in their hand and positions their hand on the side of the collection box 100 in line with their shoulder and the collection box 100 is placed in midline of user's body on the table top. The user then inserts the coins one at a time into each slot from their palm to fingers. For example, if testing the left hand, proceeding from the top left of the board to the right, then down a row from right to left, then down to the third row from left to right, and finally down to the bottom row from right to left. Of course, other suitable patterns can be utilized. The user can be instructed not to raise the elbow above the table level on which the collection box 100 sits.

As shown, the slots 112 are arranged in a predetermined configuration or pattern. The pattern of slots 112 tests the user's ability to perform palm to finger rotation, shift and translation of a small object, as well as in hand manipulation, accuracy and dexterity with functional oblique wrist motion (such as wrist extension with radial deviation and wrist flexion with ulnar deviation). The present invention also requires the user to hold multiple test objects in the hand at one time and turn the hand-wrist over to place the objects in the lid slots. This involves motion between the forearm, wrist and the hand. The present invention can be used to test the user, and can also be utilized as therapy to treat and to assess progress with functional dexterity. The pattern requires wrist motion to target small object into a designated angled slot 112 followed by another angled slot 112 which requires increased range of wrist motion while accurately placing object into targeted slot 112.

For example, in the embodiment of FIG. 1, the user starts at the top left and moves from the left to the right along the first (top) row, then moves down to the second row, moves from the right to the left along the second row, then down to the third row, moves from the left to the right along the third row, and finishes by moving down to the fourth (bottom) row and moves from the right to the left along the fourth row. At the top left, the user starts with a vertical slot 112 (i.e., extending orthogonally away from the user). The user then moves to the next adjacent slot to the right, which here is a backslash slot 112 (i.e., extending at an approximate 45° angle from the top left to the bottom right), which is followed by a forward slash slot 112 (i.e., extending from the bottom left to the top right), and finally followed by another vertical slot. Another possible slot 112 is shown at the bottom right, as a horizontal slot (i.e., extending at an approximate 90° angle from left to right with respect to the user neutral or starting hand position). However, some rows need not have vertical, forward- and/or back-slashes.

Other lids 110 can be provided beyond the one non-limiting illustrative lids in the present invention with different slot sizes and patterns which are reversible for right and left hand performance requirements. For example, FIG. 1 shows a lid 10 that does not have a handle, while FIG. 2 shows a lid 10 with a handle 116. The lids of FIGS. 1-4 can be reversed (flipped over) to provide different patterns, and the lid 10 of FIG. 1 can also be rotated on the base 120 to provide different patterns. In addition, FIG. 3 shows slots that are larger and have more of an oblong shape. Those can be utilized, for instance, with a flattened marble that is substantially wider than a U.S. penny. The slots 112 are slightly larger than the test object. For a U.S. coin, the slots 112 can be approximately one inch in length and about 0.13 inches wide and spaced from about 0.90-1.25 inches from the side walls.

FIG. 4 shows another embodiment in which the slots 112 are configured with a T-shape to receive nuts and/or bolts. Four slots are shown with the T-shape rotated from one slot to the next adjacent slot, to require the user to sweep or deviate his/her wrist to the left (counter-clockwise) and then to the right (clockwise) to properly insert the item into the slot. The slots generally extend diagonally across the board from the top left of the board to the bottom right of the board, approximately in a straight line though can be somewhat curved outward (toward the top right) slightly depending on which hand (left or right) is being tested or exercised. The first slot is shown at the top left, with the T-shape upright. The next slot is slightly below and to the right of the first slot, with the T-shape turned to the left (approximately 45 degrees counter-clockwise with respect to the first slot). That requires the user to deviate his/her wrist to the left (counter-clockwise) to insert the nut and/or bolt. The third slot is slightly to the right and left of the second slot, and is rotated to the right (about 45 degrees clockwise with respect to the first slot). That requires the user to deviate his/her wrist 90 degrees to the right (clockwise) to from the second slot. The fourth slot is at the bottom right of the lid, slightly below and to the right of the third slot. The fourth slot is 90 degrees clockwise with respect to the first slot, so that the user must deviate his/her wrist further to the right with respect to the third slot. The user can repeat the pattern more than once, and can also work the pattern from the bottom right to the top left of the lid 110. The pattern of slots requires shift, rotation and translation in hand manipulation of control objects with the wrist functional oblique range of motion. The pattern requires wrist active movement to place the control objects into the targeted slots.

The plurality of slots is a predetermined pattern established by a goniometric measurement. A goniometer is an instrument that measures an angle rotation or joint angle to a precise angular rotation. It is used by Physicians, Occupational and Physical therapists to track progress in a rehabilitation program. The axis of the goniometer is placed on the point of rotation. The stationary arm of the goniometer is held in place while a moveable arm of the goniometer is placed on the other side of the axis of motion to objectively measure joint range of motion in a degree scale. This can be particularly useful for hand and wrist stiffness after an injury, or sensorimotor recovery after a nerve injury, though can be useful to treat other injuries and issues as well.

Some patterns can be more difficult than others. Thus, the slots 112 are not randomly cut, but are specifically selected to required specific degrees or arcs of wrist motion and increase degree of difficulty between slots. The pattern designed in the present invention ensures consistent arc of wrist motion between left side and right side lids. For example, along the top row of FIGS. 1, 2, the user must move from the backslash to the forward slash slot, which requires the user to sweep or deviate their wrist from the left to the right in relation to a neutral or starting hand-wrist position.

Once the test is complete, the tester or user removes the lid 110 to the opened position. The tester or user can then count and/or remove the coins that are captured in the collection base 120 to determine the user's score.

A pilot feasibility study was done with a convenience sample of 14 non-injured participants and 13 diverse hand injured participants. Descriptive statistics are used to analyze test scores. Normative estimates were obtained from 14 right hand dominant, healthy participants in the 20-30 year old range. A 1-second difference was observed in the speed of the task between dominant and non-dominant hands. Non-injured participants dropped an average of 1.5 coins with dominant hand and 1.7 coins with non-dominant hand.

In the hand injured population net time and time with penalty, retest scores and percentages of score change indicate incremental progress towards unaffected hand baseline score with test-retest comparison. Retest scores of the hand injured population exhibit an average of 15% of change indicating a decrease time, or decreased speed, of execution. An average of 68% improvement of palm to finger shift, rotation and translation and accurate target of coins is found in the diverse hand injured population in qualitative calculation of test-retest scores.

The results of the feasibility study using the innovative targeted coin (placement) test box 100 appears to be sensitive to change in participants' ability to perform palm to finger rotation, shift and translation of a(n) coin or small object with ulnar digit stabilization and functional oblique wrist motion with greater efficiency and effectiveness. Availability of the test box 100 would enhance greater data collection, consistency of tool psychometrics, clinimetrics and refinement. Until these phases of instrument development are complete, the results obtained in this present study show encouraging values. Limitations include sample selection and size. Further qualitative and quantitative investigation may address the impact of In-Hand Manipulation (IHM) therapeutic intervention on fine motor basic self-care outcomes.

Thus, the box 100 of the present invention can be utilized to evaluate the user's arm or upper extremity in hand manipulation with wrist functional oblique motion. It can also be used for therapeutic purposes to stretch and/or exercise the user's sensorimotor system of the hand and wrist, or otherwise test and/or improve manual dexterity. Though four side walls 122-125 are shown, fewer can be provided. For instance, the front wall 122 need not be provided. And while the lid 110 is shown being slidably received in a channel, any suitable connection can be provided between the lid 110 and base 120, such as for example the lid 110 can be connected to the base 120 by one or more hinges that allow the lid 110 to be rotated or pivoted with respect to the base 120. For example, a hinge can be provided at the rear side wall 124 and the rear edge of the lid 110 so that the lid 110 can be raised at the front to allow access into the center space of the base 120 by moving the lid 110 between a closed position and an opened position.

The description and drawings of the present embodiment of the invention provided in the paper should be considered as illustrative only of the principles of the invention. The invention may be configured in a variety of ways and is not intended to be limited by the preferred embodiment. For example, an electronic weight sensor pad on the inside bottom of the base 120 can be provided to measure coin dropping timed motion studies. In an alternative embodiment, a single sensor can detect a coin from any slot. In yet another embodiment, a sensor can be fitted at each slot and a controller can be coupled with the sensors to receive a detection signal from each sensor associated with a respective slot, and determine whether or not the user has successfully inserted a coin in each successive slot and a whether or not a slot has been missed. The controller can have a processing device, output display, input (to start and reset a counter) and memory device. It can also have a counter to count the number of coins detected by the sensors, and a clock to time the overall test as well as the relative speed during the test. It can also be configured to perform a number of other operations, such as to store test results, compare test results, and associate results with a particular patient. Thus, numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A method of clinically evaluating and improving manual dexterity of a user, specifically unilateral in-hand manipulation of predetermined plurality of like-shaped control objects, comprising:
   providing the plurality of like-shaped control objects to be held in a single hand of the user;
   providing a clinical manual dexterity instrument with a lid having a plurality of like-shaped openings aligned in rows and columns, the like-shaped openings configured to a size and shape of each of the plurality of control objects and angled in relation to each other 45-90 degrees to clinically measure and/or improve manual dexterity of the user using palm-to-finger tip translation, shift and rotation of one of the plurality of control objects while simultaneously stabilizing other ones of the plurality of control objects in the ulnar palm to accurately insert the one of the plurality of control objects into one of the plurality of like-shaped openings; and,
   raising the lid off of a surface to enable the control object to pass through the plurality of like-shaped openings.

2. The method of claim 1, wherein the clinical manual dexterity instrument is closed by the lid to form an interior space, and further comprising the step of collecting by the collection base of the clinical manual dexterity instrument, the control objects sequentially passing through any of the plurality of like-shaped openings on lid in a prescribed pattern.

3. The method of claim 2, further comprising removing the lid of the clinical manual dexterity instrument and determining the number of control objects in the clinical manual dexterity instrument.

4. The method of claim 1, wherein the clinical manual dexterity instrument is an interior space therebetween with a top opening and the lid of the clinical manual dexterity instrument closes the top opening to form an opened position and a closed position.

5. The method of claim 1, wherein the control object is a coin or any small object including nut and/or bolt, button, bottle caps, pills, checkers or earrings.

6. The method of claim 1, wherein the plurality of like-shaped openings all have a same size as the like-shaped control object.

7. The method of claim 1, wherein said method obtains a clinical measurement of in-hand manipulation by timed translation, shifting and rotation of the control object based on a speed and accuracy scoring calculation.

* * * * *